United States Patent
Morsy et al.

(10) Patent No.: US 10,114,101 B2
(45) Date of Patent: Oct. 30, 2018

(54) FLOW CELL FOR BATCH AND CONTINUOUS SIMULTANEOUS ELECTROCHEMICAL AND EPR MEASUREMENTS AND A METHOD THEREOF

(71) Applicant: KING FAHD UNIVERSITY OF PETROLEUM AND MINERALS, Dhahran (SA)

(72) Inventors: Mohamed Aly Morsy, Dhahran (SA); Abdel-Nasser Metwally Kawde, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 382 days.

(21) Appl. No.: 15/081,221

(22) Filed: Mar. 25, 2016

(65) Prior Publication Data
US 2017/0276756 A1    Sep. 28, 2017

(51) Int. Cl.
G01R 33/60    (2006.01)

(52) U.S. Cl.
CPC .................................. *G01R 33/60* (2013.01)

(58) Field of Classification Search
CPC .................................................... G01R 33/60
See application file for complete search history.

(56) References Cited

U.S. PATENT DOCUMENTS

| | | | |
|---|---|---|---|
| 4,996,311 A | | 2/1991 | Moussavi et al. |
| 5,867,026 A | * | 2/1999 | Haner ............... G01R 33/307 324/300 |
| 6,391,646 B1 | | 5/2002 | Khangulov |
| 2015/0068899 A1 | * | 3/2015 | Kawde ............... G01N 24/10 204/435 |

FOREIGN PATENT DOCUMENTS

| | | |
|---|---|---|
| CN | 2283854 Y | 6/1998 |
| CN | 2283855 Y | 6/1998 |
| FR | 2 626 676 A1 | 8/1989 |
| JP | 2925948 B2 | 5/1999 |

OTHER PUBLICATIONS

"Electron Spin Resonance Spectroscopy", The Compton Group, Electrochemistry University of Oxford, http://compton.chem.ox.ac.uk/index.php?title=research&topic=esr, Nov. 28, 2014, 2 pages.

* cited by examiner

*Primary Examiner* — Patrick Assouad
*Assistant Examiner* — Haidong Zhang
(74) *Attorney, Agent, or Firm* — Oblon, McClelland, Maier & Neustadt, L.L.P.

(57) ABSTRACT

A flow cell and a method for batch and continuous simultaneous electrochemical (EC) and electron paramagnetic resonance (EPR) measurements. The flow cell includes first and second tubes with hollow interiors and the first tube is removably connected to first and second tube assemblies. The interior of the second tube contains first ends of first and second electrodes and a solution comprising an analyte. When a voltage is applied to the second electrode, the analyte undergoes a reduction or an oxidation process to generate radicals, which in turn, give rise to EPR signals.

17 Claims, 6 Drawing Sheets

FLOW CELL FOR BATCH AND CONTINUOUS SIMULTANEOUS ELECTROCHEMICAL AND EPR MEASUREMENTS AND A METHOD THEREOF

BACKGROUND OF THE INVENTION

Technical Field

The present invention relates to a flow cell for both batch and continuous simultaneous electrochemical and electron paramagnetic resonance spectroscopic measurements, and methods of using the flow cell.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

New U.S. FDA guidelines on Metabolites in Safety Testing (MIST) have led pharmaceutical companies to reassess the timing of drug metabolite studies within the development process. To facilitate effective decision making, information on metabolite identity, quantity, pharmacological, and toxicological effects is now often required at earlier stages. Oxidation is a primary route of drug metabolism, and can result in the production of reactive species that may lead to adverse effects. Studies have shown that electrochemical (EC) oxidation can be used to produce species that correspond to biological oxidative metabolites.

Electron paramagnetic resonance (EPR) spectroscopy yields incontrovertible evidence of the presence of paramagnetic intermediates (e.g. radicals) formed in oxidation processes. In addition, EPR spectroscopy sheds light on the molecular structure near the unpaired electron. Therefore, this technique may be employed to identify the paramagnetic species and help researchers elucidate the oxidation mechanism that leads biological oxidative metabolites.

A simultaneous EC-EPR technique was developed more than fifty years ago to identify paramagnetic intermediates in EC reactions (D. H. Geske, A. H. Maki, Journal of the American Chemical Society, 1960, 82, p. 2671; J. D. Wadhawan, R. G. Compton Encyclopedia of Electrochemistry, 2003, vol. 2, Wiley VCH, Germany, p. 171—each incorporated herein by reference in its entirety). A variety of EC-EPR cells have been designed to facilitate this technique (R. N. Bagchi, A. M. Bond, F. Scholz, Electroanalysis, 1.989, 1, p. 1—incorporated herein by reference in its entirety). However, these cells are either expensive or difficult to use, and the electrodes in these cells are made of platinum or silver precious metals. In addition, these cells are designed for batch monitoring and hence are incompatible with continuous measurements.

In view of the foregoing, the objective of the present disclosure is to provide an economical flow cell for batch and continuous simultaneous EC and EPR measurements.

BRIEF SUMMARY OF THE INVENTION

According to a first aspect, the present disclosure relates to a flow cell comprising: (i) a first tube with a hollow interior, a top portion and a bottom portion, (ii) a second tube forming a conduit with an inlet and an outlet, where the second tube is positioned in the hollow interior of the first tube, (iii) a first electrode with a first end positioned in the conduit, and (iv) a second electrode with a first end positioned in the conduit, where the first end of the second electrode opposes the first end of the first electrode and leaves a gap therebetween, where the bottom portion of the first tube is removably connected to a first tube assembly, the top portion of the first tube is removably connected to a second tube assembly, the inlet of the conduit is fluidly connected to at least one solution comprising an analyte, the outlet of the conduit is fluidly connected to a waste receptacle, and a second end of the first electrode is electrically connected to a measurement device and a second end of the second electrode is electrically connected to a voltage source.

In one embodiment, the first tube and the second tube are arranged to form concentric cylinders.

In one embodiment, the voltage source is a potentiostat.

In one embodiment, the first tube assembly comprises: (i) a third tube with a hollow interior and a top portion, which is removably connected to the bottom portion of the first tube, (ii) a fourth tube with a hollow interior and an exterior, where the fourth tube is positioned in the hollow interior of the third tube and the second end of the first electrode is located in the hollow interior of the fourth tube, (iii) an electro-conductive material positioned in the hollow interior of the fourth tube, where a second end of the first electrode engages the electro-conductive material, (iv) at least one inlet flow channel positioned in the hollow interior of the third tube, where the at least one inlet flow channel connects the inlet of the conduit with at least one solution comprising an analyte, (v) a wire with a first end and a second end, where the first end of the wire is positioned in the hollow interior of the fourth tube, opposing the second end of the first electrode and engages the electro-conductive material, and (vi) a first seal positioned circumferentially about the first electrode that seals the hollow interior of the fourth tube from the conduit, where the inlet flow channel and the exterior of the fourth tube secured in the hollow interior of the third tube.

In another embodiment, the second tube assembly comprises; (i) a fifth tube with a hollow interior and a bottom portion, which is removably connected to the top portion of the first tube, (ii) a sixth tube with a hollow interior and an exterior, where at least a portion of the sixth tube is positioned in the hollow interior of the fifth tube and the second electrode extends through the hollow interior of the sixth tube, (iii) an outlet flow channel positioned in the hollow interior of the fifth tube, where the outlet flow channel connects the outlet of the conduit with the waste receptacle, and (iv) a second seal positioned circumferentially about the second electrode that seals the hollow interior of the sixth tube from the conduit, where the interior of the fifth tube, the outlet flow channel and the exterior of the sixth tube are irreversibly attached to one another.

In one embodiment, the first electrode has a diameter ranging from 0.13-1.40 mm.

In one embodiment, the first tube and the second tube comprise quartz.

In one embodiment, the first tube has an inner diameter and the second tube has an inner diameter, where a ratio of the inner diameter of the first tube to the inner diameter of the second tube ranges from 2:1 to 12:1.

In one embodiment, the third tube and the fourth tube comprise quartz.

In one embodiment, the third tube has an inner diameter and the fourth tube has an inner diameter, where a ratio of the inner diameter of the third tube to the inner diameter of the fourth tube ranges from 2:1 to 12:1.

In one embodiment, the exterior of the fourth tube and the inlet flow channel are secured by epoxy in the interior of the third tube.

In one embodiment, there are two inlet flow channels each fluidly connected to a different solution.

In one embodiment, the electro-conductive material is positioned the fourth tube proximal to the conduit.

In one embodiment, the electro-conductive material is in a form of a paste or a liquid.

In one embodiment, the wire comprises copper.

In one embodiment, the fifth tube and the sixth tube comprise quartz.

In one embodiment, the fifth tube has an inner diameter and the sixth tube has an inner diameter, where a ratio of the inner diameter of the fifth tube to the inner diameter of the sixth tube ranges from 5:3 to 14:1.

In one embodiment, the inner diameter of the fifth tube is larger than an outer diameter of the first tube by 10-40%.

According to a second aspect, the disclosure relates to a method for monitoring formation of radical species with the flow cell of the first aspect. The method comprises: (i) flowing the at least one solution comprising the analyte into the conduit, (ii) positioning the flow cell within a EPR spectrometer comprising a probehead comprising a cavity, where the gap is positioned within the cavity, (iii) applying a voltage to the second end of the second electrode to form a solution comprising radical species, (iv) measuring the electrical potential at the first end of the first electrode, and (v) monitoring the formation of radical species with the EPR spectrometer.

In one embodiment, the method further comprises continuously removing the solution comprising radical species after the monitoring, where the flowing, the applying and the monitoring are performed continuously.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

Figure 5:
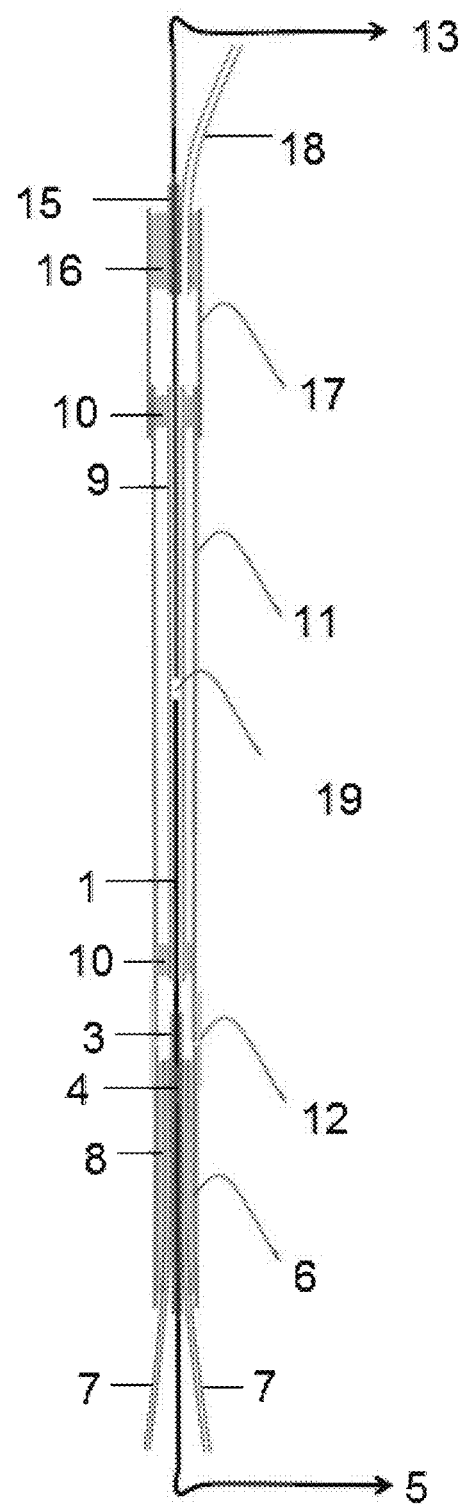
FIG. 5 is a schematic of an embodiment of the assembled flow cell.

A flow cell having removable tube assemblies for simultaneous electrochemical and electron paramagnetic resonance (EPR) spectroscopic measurements is shown in FIG. 5. The flow cell has: (i) a first tube 11 with a hollow interior, a top portion and a bottom portion, (ii) a second tube 9 forming a conduit with an inlet which is fluidly connected to a solution and an outlet which is fluidly connected to a waste receptacle, and the second tube is positioned in the hollow interior of the first tube, (iii) a first end of a first electrode 1 positioned in the conduit, and (iv) a first end of a second electrode 13 positioned in the conduit such that the first end of the second electrode opposes the first end of the first electrode and leaves a gap 19 therebetween, while a second end of the first electrode is electrically connected to a measurement device and a second end of the second electrode is electrically connected to a voltage source. The flow cell is arranged in a two-electrode configuration that allows for the reduction or oxidation of a compound that is placed within the flow cell when a voltage is applied to the second electrode, such as from a battery or preferably a potentiostat. The flow cell can also be placed within a cavity of an EPR spectrometer to analyze free radicals.

The first tube may be made of a material comprising fused quartz which may be electrically fused quartz, flame fused quartz, or preferably, synthetic fused silica. In a preferred embodiment, the first tube is made of synthetic fused silica. An inner diameter of the first tube may range from 1-6 mm, preferably 2-5 mm, more preferably 2-4 mm. A thickness of a wall of the first tube may range from 0.1-1 mm, preferably 0.4-0.9 mm, more preferably 0.5-0.8 mm. An outer diameter of the first tube may range from 1.2-8 mm, preferably 2.2-7 mm, preferably 2.2-6 mm. A height of the first tube may range from 30-80 mm, preferably 40-70 mm, more preferably 40-50 mm.

The second tube may be made of the aforementioned materials for the first tube. Preferably, the second tube is made of synthetic fused silica. A diameter of the conduit, which is also an inner diameter of the second tube, may range from 0.5-1.5 mm, preferably 0.8-1.2 mm, more preferably about 1 mm. A thickness of a wall of the second tube may range from 0.1-1 mm, preferably 0.3-0.7 mm, more preferably 0.3-0.5 mm. An outer diameter of the second tube may range from 0.7-3.5 mm, preferably 0.7-2.6 mm, preferably 0.7-2.5 mm. A height of the conduit, which is also a height of the second tube, may range from 30-70 mm, preferably 40-60 mm, more preferably 40-45 mm.

A ratio of the inner diameter of the first be to the inner diameter of the second tube ranges from 2:1 to 12:1, preferably 2:1 to 7:1, more preferably 2:1 to 4:1.

In a preferred embodiment, the first and second tubes form concentric cylinders such that a longitudinal centerline of the first tube overlaps with a longitudinal centerline of the second tube. This arrangement may be achieved by employing at least one concentric member 10 positioned circumferentially about an exterior of the second tube and in the interior of the first tube. The concentric member may be a gasket, or preferably an O-ring. Preferably, there are two O-rings, one positioned on a lower end of the second tube, and one positioned on an upper end of the second tube so as to leave the gap unobstructed for EPR analysis. A distance between the first end of the first electrode and the first end of the second electrode, and hence the size of the gap, ranges from 0.1-0.5 cm, preferably 0.1-0.4 cm, more preferably 0.2-0.4 cm. A shortest vertical distance measured between the centers of the O-rings ranges from 0.5-4 cm, preferably 1-3.5 cm, more preferably 1-3 cm. The gasket may be preferably made of a chemical-resistant material, such as Viton® or Teflon®, which can withstand organic solvents and corrosive chemicals such as acids and bases.

The first end of first electrode is positioned within the interior of the second tube, preferably in a middle portion of the second tube, and the second end of the first electrode is located in the interior of the fourth tube. In a preferred embodiment, the first electrode is a working electrode, which may be made from at least on material, including but not limited to base metals, such as copper, precious metals, such as gold, silver or platinum, and allotropes of carbon. Preferably, the first electrode is made from graphite, an allotrope of carbon. In a preferred embodiment, the first electrode is a black graphite pencil lead. In this regard, the graphite pencil lead is typically classified in terms of hardness grades. Hardness grades are associated on a hardness scale with the letter H or B or a combination of both, H B. Graphite pencil lead of grades B, H or preferably HB, may be used. A length of the pencil lead may range from 20-50 mm, preferably 25-50 mm, more preferably 30-50 mm. A diameter of the pencil lead may range from 0.13-1.40 mm, preferably 0.3-1 mm, more preferably 0.5-0.7 mm.

The first end of the second electrode is positioned within the interior of the second tube, opposing the first end of the first electrode, and preferably in a middle position of the second tube, more preferably at 40-50% of the height of the second tube. The second end of the second electrode is connected to a voltage source. The second electrode may be a reference electrode which is made from silver and silver chloride, for example, or other suitable materials, such as mercury and mercury(I) chloride, copper and copper(II) sulfate, depending on the application.

Figure 1:
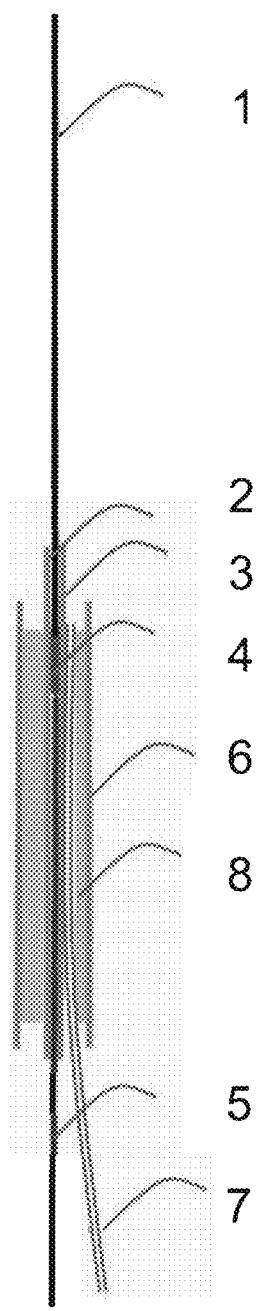
FIG. 1 is a schematic of an embodiment of the first tube assembly of the flow cell.
Figure 2:
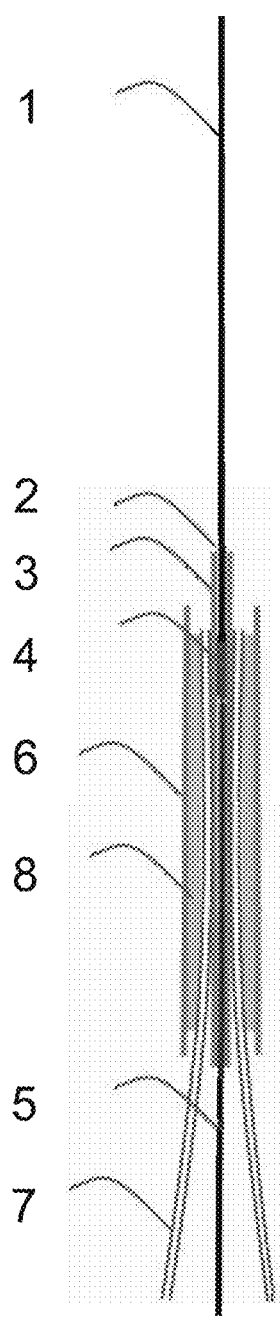
FIG. 2 is a schematic of another embodiment of the first tube assembly of the flow cell.
Figure 3:
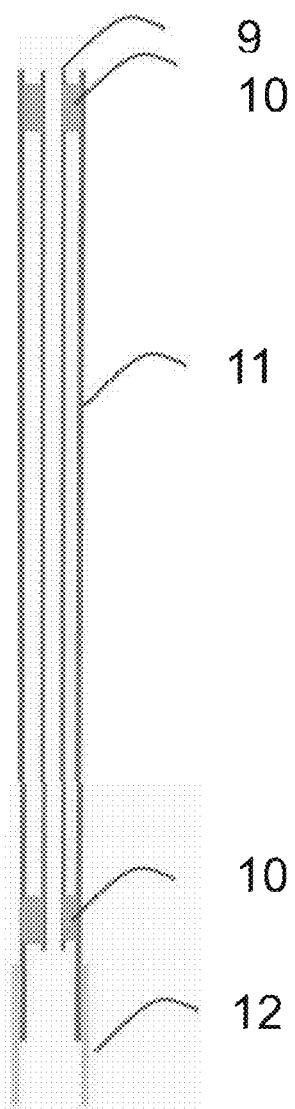
FIG. 3 is a schematic of an embodiment that shows an arrangement of the second tube within the first tube.
Figure 4:
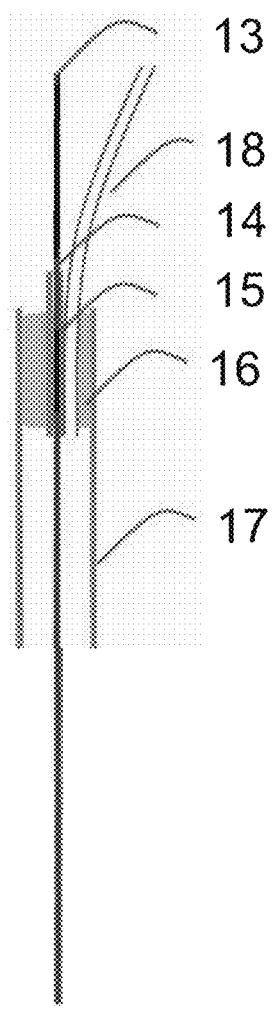
FIG. 4 is a schematic of an embodiment of the second tube assembly of the flow cell.

The bottom portion of the first tube is removably connected to a first tube assembly (embodiments of the first tube assembly are shown in FIGS. 1 and 2) while the top portion of the first tube is removably connected to a second tube assembly (FIG. 3). Specifically, the bottom portion of the first tube is removably connected to a top portion of a third tube 6. In a preferred embodiment, the tubes are connected by a straight tube connector 12 which has two opposing ends. More preferably, the tube connector has an inner diameter larger than the outer diameters of the first and third tubes. For example, the inner diameter of the tube connector may range from 1.5-10 mm, preferably 2.5-8 mm, preferably 2.5-7 mm. In one embodiment, the first and third tubes are inserted into the opposing ends of the tube connector. The tube connector may be made of a material comprising polypropylene, polyethylene, polyvinyl chloride (PVC) and polytetrafluoroethylene (PTFE). In a preferred embodiment, the tube connector is in the form of flexible tubing (e.g. Tygon tubing).

Embodiments of the first tube assembly are shown in FIGS. 1 and 2. The first tube assembly comprises a third tube 6 with a hollow interior and a top portion, and a fourth tube 3 with a hollow interior and is positioned in the hollow interior of the third tube. In a preferred embodiment, the third tube and the fourth tube form concentric cylinders.

The third tube may be made of a material comprising glass or fused quartz which may be electrically fused quartz, flame fused quartz, or preferably, synthetic fused silica. In a preferred embodiment, the third tube is made of synthetic fused silica. The dimensions of the third tube may be the same as the dimensions of the first tube.

The fourth tube may be made of the aforementioned materials for the third tube. Preferably, the fourth tube is made of synthetic fused silica. An inner diameter of the fourth tube may range from 0.5-1.5 mm, preferably 0.8-1.2 mm, more preferably about 1 mm. A thickness of a wall of the fourth tube may range from 0.1-1 mm, preferably 0.3-0.7 mm, more preferably 0.3-0.5 mm. An outer diameter of the fourth tube may range from 0.7-3.5 mm, preferably 0.5-3.0 mm, preferably 0.5-2.5 mm. A height of the fourth tube may range from 30-80 mm, preferably 40-70 mm, more preferably 40-50 mm.

A ratio of the inner diameter of the third tube to the inner diameter of the fourth tube ranges from 2:1 to 12:1, preferably 2:1 to 7:1, more preferably 2:1 to 4:1.

The first electrode extends from the second tube, through a first seal 2 and the second end of the first electrode is located in an upper portion of the interior of the fourth tube.

The first seal is positioned circumferentially about the first electrode and in the upper portion of the fourth tube, closing off the aperture at the top of the fourth tube and prevents a liquid flow from the conduit into fourth tube. The first seal may be made from a number of suitable materials, including but are not limited to, plastic, rubber, or thread seal tape, commonly referred to as "Teflon® tape". Thread seal tape is typically a polytetrafluoroethylene (PTFE) film common for use in sealing pipe threads and tubes. In another embodiment, the first seal is a glue.

An electro-conductive material 4 is deposited within the upper portion of the interior of the fourth tube. The electro-conductive material carries the potential from the first electrode to a wire 5. The electro-conductive material may be of any suitable form, such as in the form of either a conducting paste or a conducting liquid. The electro-conductive material may also be made from a number of various materials, including a carbon paste or liquid mercury. The height of the electro-conductive material in the fourth tube may range from 1-15 mm, preferably 3-10 mm, more preferably 3-8 mm. The second end of the first electrode engages, or is preferably buried in, the electro-conductive material. A depth of the first electrode in the electro-conductive material ranges from 0.1-2 mm, preferably 0.1-1.5 mm, more preferably 0.5-1 mm.

The wire 5 originates from outside the fourth tube, extends through the hollow interior into the upper portion of the fourth tube to engage the electro-conductive material. In a preferred embodiment, the first end of the wire is buried in the electro-conductive material at a depth ranging from 0.1-2 mm, preferably 0.1-1.5 mm, more preferably 0.5-1 mm. The wire communicates the potential from the first electrode that is carried by the electro-conductive material to a measurement device. The wire may be made from a number of various metals, including but are not limited to copper, aluminum and gold. In a preferred embodiment, the wire is made of copper. A diameter of the wire may range from 0.1-1.40 mm, preferably 0.3-1 mm, more preferably 0.5-0.7 mm. As the wire is engaged with the electro-conductive material, various electrochemical measurements can be taken and determined, such as values of potential or current that act upon the first electrode. Non-limiting examples of a measurement device include a potentiostat, an ammeter, a voltmeter or a multi-meter.

There is at least one inlet flow channel 7 positioned in the hollow interior of the third tube. There may be one (FIG. 1), or preferably, two inlet flow channels (FIG. 2). The inlet flow channel connects the inlet of the conduit and fills the gap with at least one solution comprising an analyte and each flow channel may connect to a different solution. Each different solution may comprise a different analyte or the same analyte at varying concentrations. The flow channel may take a form of a tubing, preferably a flexible tubing. An outlet of the flow channel is positioned in the hollow interior of the third tube, preferably near the top portion of the third tube, and an inlet of the flow channel is connected to a syringe containing the solution, a vessel containing the solution or a pump which pumps the solution from a vessel into the flow cell. The flow channel has an external diameter ranging from 0.1-2 mm, preferably 0.3-1.5 mm, more preferably 0.5-1 mm. An internal diameter of the flow channel ranges from 0.05-0.8 mm, preferably 0.1-0.5 mm, more preferably 0.1-0.3 mm. The flow channel may be made of a material compatible with the solution. Non-limiting examples of such material include polypropylene, polyethylene, polyvinyl chloride (PVC) and polytetrafluoroethylene (PTFE). Preferably, the inlet flow channel is made of PTFE.

The solution may be an electrolyte solution comprising an analyte, which refers to the substance to be analyzed or tested. The electrolyte may be a buffer, an acid, or a base in an aqueous or non-aqueous solution. Non-limiting examples of electrolytes include a solution of sulfuric acid, a solution of sodium hydroxide and a solution of potassium hydroxide. Preferably, the electrolyte is a solution of sulfuric acid with a concentration ranging from 0.05-0.5 M, preferably 0.5-0.3 M, more preferably 0.05-0.2 M. As used herein, the term "analyte" refers to the compound of interest that will be analyzed by an EPR spectrometer and an electrochemical process. Non-limiting examples of the analyte include carotenoids and therapeutic pharmaceutical compounds such as Ketoconazole, a common drug for the treatment of fungal infections of the mouth, skin, and urinary tract. A concentration of the analyte may range from 0.05-0.5 mM, preferably 0.1-0.4 mM, more preferably 0.1-0.3 mM. In one embodiment with two inlet flow channels, a first inlet flow channel may be fluidly connected to the electrolyte while a second flow channel may be fluidly connected to a concentrated solution of an analyte.

The inlet flow channel and the exterior of the fourth tube are irreversibly attached to one another in the interior of the third tube, and are preferably secured by an epoxy glue 8, which also seals a bottom aperture of the third tube to prevent leakage of the solution from the flow cell. The inlet flow channel and the exterior of the fourth tube may be secured by a super glue and/or a sealant.

The second tube assembly comprises a fifth tube 17 with a hollow interior and a sixth tube 15 with a hollow interior, where at least a portion of the sixth tube is positioned in the hollow interior of the fifth tube. In a preferred embodiment, the sixth tube is positioned in an upper portion of the fifth tube. In another preferred embodiment, a longitudinal centerline of the fifth tube overlaps with a longitudinal centerline of the sixth tube.

The fifth tube may be made of a material comprising polypropylene, polyethylene, polyvinyl chloride (PVC), polytetrafluoroethylene (PTFE), glass or fused quartz which may be electrically fused quartz, flame fused quartz, or preferably, synthetic fused silica. In a preferred embodiment, the fifth tube is made of polyethylene. The dimensions of the fifth tube may be the same as the dimensions for the first tube. In a preferred embodiment, the inner diameter of the fifth tube ranges from 1.5-10 mm, preferably 2.5-8 mm, preferably 2.5-7 mm. More preferably, the inner diameter of the fifth tube is larger than an outer diameter of the first tube by 0.1-2 mm, preferably 0.1-1.5 mm, more preferably 0.1-1 mm so that the hollow interior of the fifth tube can accommodate an upper portion of the first tube, preferably in a removable manner. The inner diameter of the fifth tube may be larger than an outer diameter of the first tube by 10-40%, preferably 10-30%, more preferably 10-20% relative to the outer diameter of the first tube. In another embodiment, the top exterior portion of the first tube has male screw threads that are compatible with female screw threads on the interior bottom portion of fifth tube. In another embodiment, the first and fifth tubes are connected by a straight tube connector with two opposing ends. More preferably, the tube connector has an inner diameter larger than the outer diameters of the first and fifth tube. For example, the inner diameter of the tube connector may range from 1.5-11 mm; preferably 2.5-9 mm, preferably 2.5-8 mm. In one embodiment, the first and fifth tubes are inserted into the opposing ends of the tube connector. The tube connector may be made of a material comprising polypropylene, polyethylene, polyvinyl chloride (PVC) and polytetrafluoroethylene (PTFE). In a preferred embodiment, the tube connector is in the form of flexible tubing (e.g. Tygon tubing).

The sixth tube may be a capillary glass tube or made of the aforementioned materials for the fourth tube. The dimensions of the sixth tube may be the same as the dimensions of the fourth tube. In a preferred embodiment, the length of the sixth tube is 10-40 mm, preferably 10-30 mm, more preferably 10-20 mm.

A ratio of the inner diameter of the fifth tube to the inner diameter of the sixth tube ranges from 5:3 to 14:1, preferably 5:3 to 7:1, more preferably 5:3 to 4:1.

The second end of the second electrode extends through an upper portion of the sixth tube, through a second seal 14 and is connected to a voltage source. The second seal is positioned circumferentially about the second electrode and in an upper p on of the sixth tube, closing off the aperture at the top of the sixth tube to prevent leakage of the solution from the conduit into the sixth tube. The second seal may be made from the same material as the first seal.

There is an outlet flow channel 18 positioned in the hollow interior of the fifth tube. The outlet flow channel connects the outlet of the conduit to a waste receptacle. The flow channel may take a form of a tubing, preferably a flexible tubing. An inlet of the outlet flow channel is positioned in the hollow interior of the fifth tube, preferably near the top portion of the fifth tube, and an outlet of the outlet flow channel terminates in a waste receptacle such as a beaker, a flask or a carboy. The flow channel has an external diameter ranging from 0.1-2 mm, preferably preferably 0.3-1.5 mm, more preferably 0.5-1 mm. An internal diameter of the flow channel ranges from 0.05-0.8 mm, preferably 0.1-0.5 mm, more preferably 0.1-0.3 mm. The flow channel may be made of a material compatible with the solution. The outlet flow channel may be made of the same material as the inlet flow channel. Preferably, the outlet flow channel is made of PTFE.

The outlet flow channel and the exterior of the sixth tube are irreversibly attached to one another in the interior of the fifth tube, and are preferably secured by an epoxy glue 16, which also seals a top aperture of the fifth tube to prevent leakage of the solution from the flow cell. The outlet flow channel and the exterior of the sixth tube may also be secure by a super glue.

According to the second aspect, this disclosure relates to a method of employing the flow cell in batch and continuous EC-EPR studies. The method may be performed at a temperature ranging from 4-60° C., preferably 4-40° C., more preferably 4-30° C. The method comprises flowing at least one solution comprising an analyte into the conduit to fill the gap. In a batch experiment, the volume of the solution ranges from 10-200 preferably 20-150 μL, more preferably 40-120 μL. The solution may be introduced from the inlet flow channel into the conduit from a syringe or a vessel. In one embodiment, the inlet flow channel is connected directly to the reaction vessel and the solution flows into conduit by gravity. The flow may be controlled by a valve, such as a stopcock. An outlet of the outlet flow channel is sealed to prevent the solution from leaking from the assembled flow cell. The outlet may be sealed by a stopper and/or a pinch clamp.

In a continuous monitoring embodiment, a solution comprising radical species is removed after the monitoring and the conduit is re-filled with a fresh solution comprising the analyte. A pump, which is fluidly connected to a reaction vessel containing the solution, may be employed to feed the solution into the conduit. The flow rate of the solution may range from 0.05-2 ml/min, preferably 0.1-1.5 ml/min, more preferably 0.1-0.5 min. Non-limiting examples of the pump include a peristaltic pump, a piston pump and a syringe pump. In a continuous monitoring embodiment, the outlet of the outlet flow channel is left open so that the solution comprising radical species can be collected in a waste receptacle such as a beaker, a flask or a carboy.

The flow cell is positioned within an EPR spectrometer comprising a probehead comprising a cavity. Preferably, the gap is positioned within the cavity such that the center of the gap coincides with the center of the cavity.

A voltage is applied to the second end of the second electrode to form the solution comprising radical species. The applied voltage may range from 0.4-1 V, preferably 0.5-0.8 V, more preferably 0.55-0.65 V. When voltage is applied to the second electrode, the generated potential enters the solution and initiates a reduction or an oxidation of the analyte at the first electrode. The voltage may be applied for a period of time to result in an accumulation potential, which acts upon the first electrode. The voltage may be applied for a duration ranging from 30-300 seconds, preferably 50-200 seconds, more preferably 60-120 seconds. A rest period ranging from 2-60 s, preferably 2-40 s, more preferably 2-30 s may ensue. The electro-conductive material communicates the accumulation potential to the wire. The measurement device, in communication with the wire, measures the potential and current acting upon the first electrode. In a preferred embodiment, the measurement device and the voltage source are the same device, being a potentiostat.

After the voltage is applied, the solution is monitored for the presence of radical species. The operations of the EPR spectrometer and the relevant spectrum processing software are well known to those skilled in the art. A spectrum may be obtained intervals ranging from 60-300 seconds, preferably 60-180 seconds, more preferably 60-120 seconds in the presence of the accumulation potential. In another embodiment, a spectrum is obtained in the absence of an applied voltage.

The present embodiments are being described with reference to specific example embodiments and are included to illustrate but not limit the scope of the disclosure or the claims.

EXAMPLE

Figure 6:
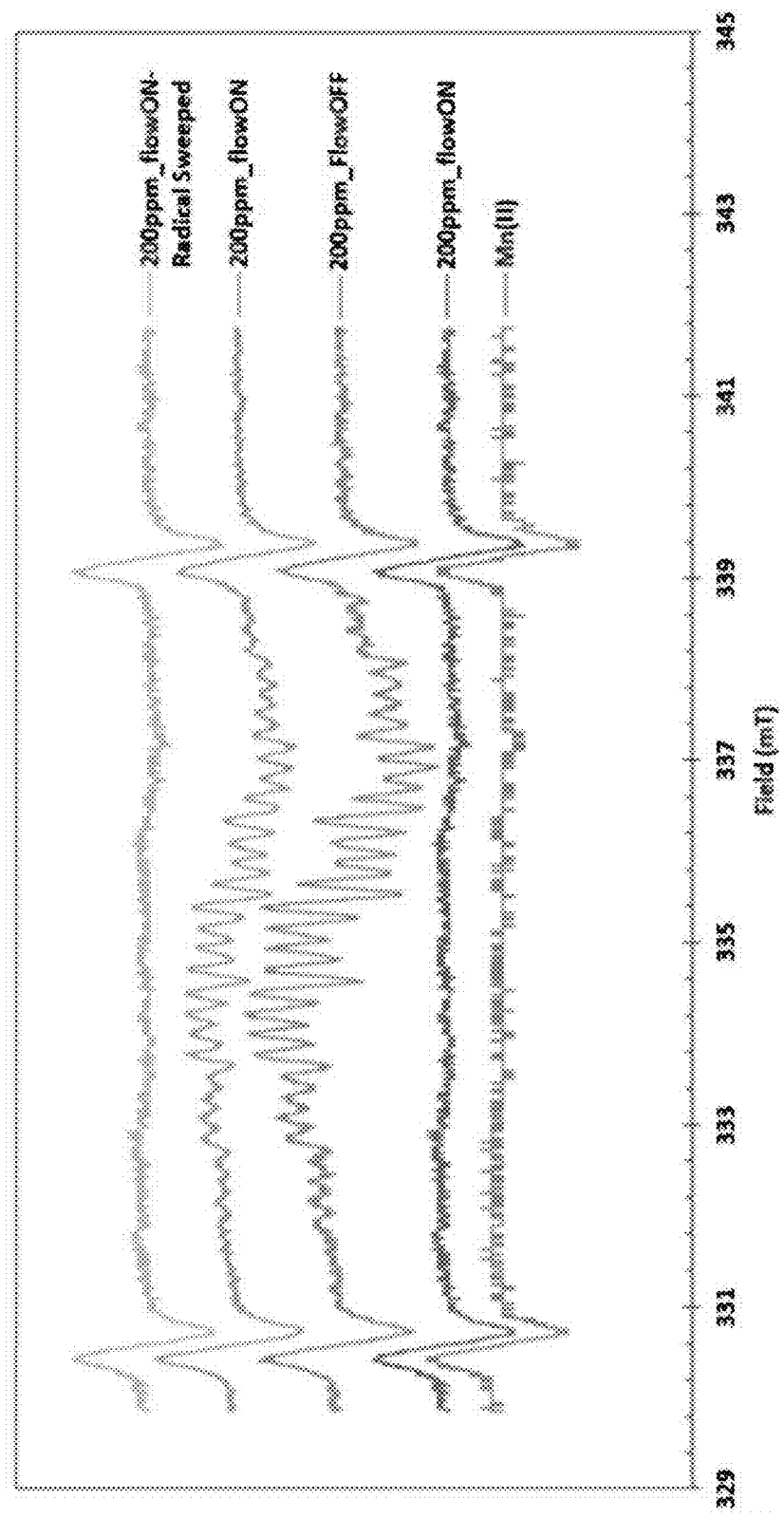
FIG. 6 is an overlay of electron paramagnetic resonance spectra obtained during the oxidation of Ketoconazole (200 mg/L) in 0.1 M sulfuric acid at +0.6 V accumulation potential with a flow ON-OFF-ON from bottom to top using a working electrode (graphite pencil lead) and a Ag/AgCl auxiliary electrode in a two-electrode electrochemical cell system.

A pharmaceutical drug, Ketoconazole (200 mg/L), was mixed with a 0.1 M sulfuric acid electrolyte solution and oxidized at an accumulation potential of +0.6 V. The first electrode was a graphite pencil lead and the reference electrode was a Ag/AgCl electrode. FIG. 6 shows an overlay of electron paramagnetic resonance (EPR) spectra obtained when the voltage was turned on (second spectrum from the bottom), then turned off (third spectrum from the bottom), and then turned on again (fourth spectrum from the bottom). When a sample of Ketoconazole was oxidized to form radicals comprising unpaired electrons, the radicals generated EPR signals that were in a range of 333 milliTeslas (mT) and 338 mT. The electrolyte solution contained Mn(II) as a reference and the satellite peaks of Mn(II) are seen in FIG. 6.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting the scope of the invention, as well as other claims. The disclosure, including any readily discernible variants of the teachings herein, defines, in part, the scope of the foregoing claim terminology such that no inventive subject matter is dedicated to the public.

The invention claimed is:
1. A flow cell, comprising:
  a first tube with a hollow interior, a top portion and a bottom portion;
  a second tube forming a conduit with an inlet and an outlet, wherein the second tube is positioned in the hollow interior of the first tube;
  a first electrode with a first end positioned in the conduit; and
  a second electrode with a first end positioned in the conduit, wherein the first end of the second electrode opposes the first end of the first electrode and leaves a gap therebetween;
  wherein the bottom portion of the first tube is removably connected to a first tube assembly, the top portion of the first tube is removably connected to a second tube assembly, the inlet of the conduit is fluidly connected to at least one solution comprising an analyte, the outlet of the conduit is fluidly connected to a waste receptacle, and a second end of the first electrode is electrically connected to a measurement device and a second end of the second electrode is electrically connected to a voltage source;
  wherein the first tube assembly comprises:
    a third tube with a hollow interior and a top portion, which is removably connected to the bottom portion of the first tube;
    a fourth tube with a hollow interior and an exterior, wherein the fourth tube is positioned in the hollow interior of the third tube and the second end of the first electrode is located in the hollow interior of the fourth tube;
    an electro-conductive material positioned in the hollow interior of the fourth tube, wherein a second end of the first electrode engages the electro-conductive material;
    at least one inlet flow channel positioned in the hollow interior of the third tube, wherein the at least one inlet flow channel connects the inlet of the conduit with the at least one solution comprising the analyte;
    a wire with a first end and a second end, wherein the first end of the wire is positioned in the hollow interior of the fourth tube, opposing the second end of the first electrode and engages the electro-conductive material; and a first seal positioned circumferentially about the first electrode and seals the hollow interior of the fourth tube from the conduit;

wherein the inlet flow channel and the exterior of the fourth tube are secured in the hollow interior of the third tube.

2. The flow cell of claim 1, wherein the first tube and the second tube are arranged to form concentric cylinders.

3. The flow cell of claim 1, wherein the voltage source is a potentiostat.

4. The flow cell of claim 1, wherein the second tube assembly comprises:

a fifth tube with a hollow interior and a bottom portion, which is removably connected to the top portion of the first tube;

a sixth tube with a hollow interior and an exterior, wherein at least a portion of the sixth tube is positioned in the hollow interior of the fifth tube and the second electrode extends through the hollow interior of the sixth tube;

an outlet flow channel positioned in the hollow interior of the fifth tube, wherein the outlet flow channel connects the outlet of the conduit with the waste receptacle; and a second seal positioned circumferentially about the second electrode and seals the hollow interior of the sixth tube from the conduit;

wherein the outlet flow channel and the exterior of the sixth tube are secured in the hollow interior of the fifth tube.

5. The flow cell of claim 1, wherein the first electrode has a diameter ranging from 0.13-1.40 mm.

6. The flow cell of claim 1, wherein the first tube and the second tube comprise quartz.

7. The flow cell of claim 1, wherein the first tube has an inner diameter and the second tube has an inner diameter, where a ratio of the inner diameter of the first tube to the inner diameter of the second tube ranges from 2:1 to 12:1.

8. The flow cell of claim 1, wherein the third tube and the fourth tube comprise quartz.

9. The flow cell of claim 1, wherein the third tube has an inner diameter and the fourth tube has an inner diameter, where a ratio of the inner diameter of the third tube to the inner diameter of the fourth tube ranges from 2:1 to 12:1.

10. The flow cell of claim 1, wherein the exterior of the fourth tube and the inlet flow channel are secured by epoxy in the interior of the third tube.

11. The flow cell of claim 1, wherein there are two inlet flow channels each fluidly connected to a different solution.

12. The flow cell of claim 1, wherein the electro-conductive material is positioned in the fourth tube proximal to the conduit.

13. The flow cell of claim 1, wherein the electro-conductive material is in a form of a paste or a liquid.

14. The flow cell of claim 1, wherein the wire comprises copper.

15. The flow cell of claim 4, wherein the fifth tube and the sixth tube comprise quartz.

16. The flow cell of claim 4, wherein the fifth tube has an inner diameter and the sixth tube has an inner diameter, where a ratio of the inner diameter of the fifth tube to the inner diameter of the sixth tube ranges from 5:3 to 14:1.

17. The flow cell of claim 4, wherein the inner diameter of the fifth tube is larger than an outer diameter of the first tube by 10-40%.

* * * * *